(12) United States Patent
Yamaguchi

(10) Patent No.: US 7,675,017 B2
(45) Date of Patent: Mar. 9, 2010

(54) IMAGE CAPTURING SYSTEM, IMAGE CAPTURING METHOD, AND RECORDING MEDIUM

(75) Inventor: Hiroshi Yamaguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/266,357

(22) Filed: Nov. 6, 2008

(65) Prior Publication Data

US 2009/0114803 A1    May 7, 2009

(30) Foreign Application Priority Data

Nov. 7, 2007 (JP) ............................. 2007-290101
Oct. 21, 2008 (JP) ............................. 2008-271324

(51) Int. Cl.
  *G01J 1/58* (2006.01)
  *G01B 11/22* (2006.01)
  *H04N 5/228* (2006.01)

(52) U.S. Cl. ............... 250/208.1; 250/226; 250/339.05; 600/109

(58) Field of Classification Search .............. 250/208.1, 250/226, 339.05; 600/160, 178, 180, 109
See application file for complete search history.

(56) References Cited

U.S. PATENT DOCUMENTS

| 5,804,827 | A * | 9/1998 | Akagawa et al. ........ 250/370.06 |
| 6,293,911 | B1 * | 9/2001 | Imaizumi et al. ............ 600/160 |
| 6,448,545 | B1 | 9/2002 | Chen |
| 7,172,553 | B2 * | 2/2007 | Ueno et al. ................. 600/160 |
| 7,274,393 | B2 * | 9/2007 | Acharya ..................... 348/273 |
| 2002/0147383 | A1 | 10/2002 | Weber et al. |
| 2003/0001093 | A1 * | 1/2003 | Wood ........................ 250/332 |
| 2003/0078477 | A1 | 4/2003 | Kang et al. |
| 2006/0268402 | A1 | 11/2006 | Eustergerling et al. |

(Continued)

FOREIGN PATENT DOCUMENTS

EP    2006/116847  A1    11/2006

(Continued)

OTHER PUBLICATIONS

EP Communication, dated Feb. 9, 2009, issued in corresponding EP Application No. 08019459.0, 8 pages.

*Primary Examiner*—John R Lee
(74) *Attorney, Agent, or Firm*—Sughrue Mion, PLLC

(57) ABSTRACT

Provided is an image capturing system, including an image capturing section that includes a plurality of first light receiving elements that receive light in a specified wavelength region and light in a first wavelength region, which is different from the specified wavelength region, and a plurality of second light receiving elements that receive light in a second wavelength region, which is different from the specified wavelength region; and a control section that controls a spectrum of the light received by the plurality of first light receiving elements. The control section, at a first timing, causes the plurality of first light receiving elements to receive light in a wavelength region including the first wavelength region from a subject and causes the plurality of second light receiving elements to receive light in the second wavelength region and, at a second timing, causes the plurality of first light receiving elements to receive light in a wavelength region including the specified wavelength region from the subject and causes the plurality of second light receiving elements to receive light in the second wavelength region.

18 Claims, 9 Drawing Sheets

U.S. PATENT DOCUMENTS

| | | | |
|---|---|---|---|
| 2008/0309924 A1* | 12/2008 | Jung et al. | 356/73 |
| 2009/0020709 A1* | 1/2009 | Yamaguchi et al. | 250/458.1 |
| 2009/0114799 A1* | 5/2009 | Maeda | 250/201.1 |
| 2009/0114803 A1* | 5/2009 | Yamaguchi | 250/226 |
| 2009/0122152 A1* | 5/2009 | Yamaguchi et al. | 348/222.1 |
| 2009/0124854 A1* | 5/2009 | Yamaguchi et al. | 600/109 |
| 2009/0147096 A1* | 6/2009 | Yamaguchi et al. | 348/222.1 |
| 2009/0147998 A1* | 6/2009 | Yamaguchi et al. | 382/106 |
| 2009/0147999 A1* | 6/2009 | Maeda et al. | 382/106 |
| 2009/0159776 A1* | 6/2009 | Maeda et al. | 250/201.1 |

FOREIGN PATENT DOCUMENTS

| | | |
|---|---|---|
| JP | 2004-329583 A | 11/2004 |
| JP | 2006-043289 A | 2/2006 |

* cited by examiner

IMAGE CAPTURING SYSTEM, IMAGE CAPTURING METHOD, AND RECORDING MEDIUM

CROSS REFERENCE TO RELATED APPLICATION

The present application claims priority from a Japanese Patent Applications No. 2007-290101 filed on Nov. 7, 2007 and No. 2008-271324 filed on Oct. 21, 2008, the contents of which are incorporated herein by reference.

BACKGROUND

1. Technical Field

The present invention relates to an image capturing system, an image capturing method, and a program. In particular, the present invention relates to an image capturing system and an image capturing method for capturing an image, and to a program used by the image capturing system.

2. Related Art

A known electronic endoscope includes a plurality of light receiving elements arranged in a matrix on a single semiconductor substrate, and is provided with a solid image capturing element on a tip thereof that can obtain visible light image information and fluorescent light image information, as disclosed in Japanese Patent Application Publication No. 2004-329583. An endoscope apparatus is known that creates a fluorescent observation image using (i) an image signal of a subject captured by an image capturing means when a light source irradiates the subject with illumination light and (ii) an image signal of a subject captured by an image capturing means when a light source irradiates the subject with excitation light, as disclosed in Japanese Patent Application Publication No. 2006-43289.

In the electronic endoscope described above, the illumination light and the excitation light are emitted sequentially with prescribed time cycles, so that the illumination light image cannot be captured while the excitation light is being emitted. In the endoscope apparatus described above captures images as red, green, and blue light is emitted sequentially, and therefore cannot obtain a visible light image with a single image capture. For these reasons, the devices disclosed in the above patent documents cannot capture images at a high frame rate, such as those viewed by a doctor, and often skip frames in a resulting video. Therefore, this video appears choppy to the viewer.

SUMMARY

Therefore, it is an object of an aspect of the innovations herein to provide an image capturing system, an image capturing method, and a recording medium, which are capable of overcoming the above drawbacks accompanying the related art. The above and other objects can be achieved by combinations described in the independent claims. The dependent claims define further advantageous and exemplary combinations of the innovations herein.

According to a first aspect related to the innovations herein, one exemplary image capturing system may include: an image capturing section that includes a plurality of first light receiving elements that receive light in a specified wavelength region and light in a first wavelength region, which is different from the specified wavelength region, and a plurality of second light receiving elements that receive light in a second wavelength region, which is different from the specified wavelength region; and a control section that controls a spectrum of the light received by the plurality of first light receiving elements. The control section, at a first timing, causes the plurality of first light receiving elements to receive light in a wavelength region including the first wavelength region from a subject and causes the plurality of second light receiving elements to receive light in the second wavelength region and, at a second timing, causes the plurality of first light receiving elements to receive light in a wavelength region including the specified wavelength region from the subject and causes the plurality of second light receiving elements to receive light in the second wavelength region.

According to a second aspect related to the innovations herein, one exemplary image capturing method, may include: having a plurality of first light receiving elements that receive light in a specified wavelength region and light in a first wavelength region, which is different from the specified wavelength region, and a plurality of second light receiving elements that receive light in a second wavelength region, which is different from the specified wavelength region; and controlling a spectrum of the light received by the plurality of first light receiving elements. The controlling involves, at a first timing, causing the plurality of first light receiving elements to receive light in a wavelength region including the first wavelength region from a subject and causing the plurality of second light receiving elements to receive light in the second wavelength region and, at a second timing, causing the plurality of first light receiving elements to receive light in a wavelength region including the specified wavelength region from the subject and causing the plurality of second light receiving elements to receive light in the second wavelength region.

According to a third aspect related to the innovations herein, one exemplary recording medium may include a computer readable medium storing thereon a program for use by an image capturing system, the program causing the image capturing system to function as: an image capturing section including a plurality of first light receiving elements that receive light in a specified wavelength region and light in a first wavelength region, which is different from the specified wavelength region, and a plurality of second light receiving elements that receive light in a second wavelength region, which is different from the specified wavelength region; and a control section that controls a spectrum of the light received by the plurality of first light receiving elements and the plurality of second light receiving elements and that, at a first timing, causes the plurality of first light receiving elements to receive light in a wavelength region including the first wavelength region from a subject and causes the plurality of second light receiving elements to receive light in the second wavelength region and, at a second timing, causes the plurality of first light receiving elements to receive light in a wavelength region including the specified wavelength region from the subject and causes the plurality of second light receiving elements to receive light in the second wavelength region.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
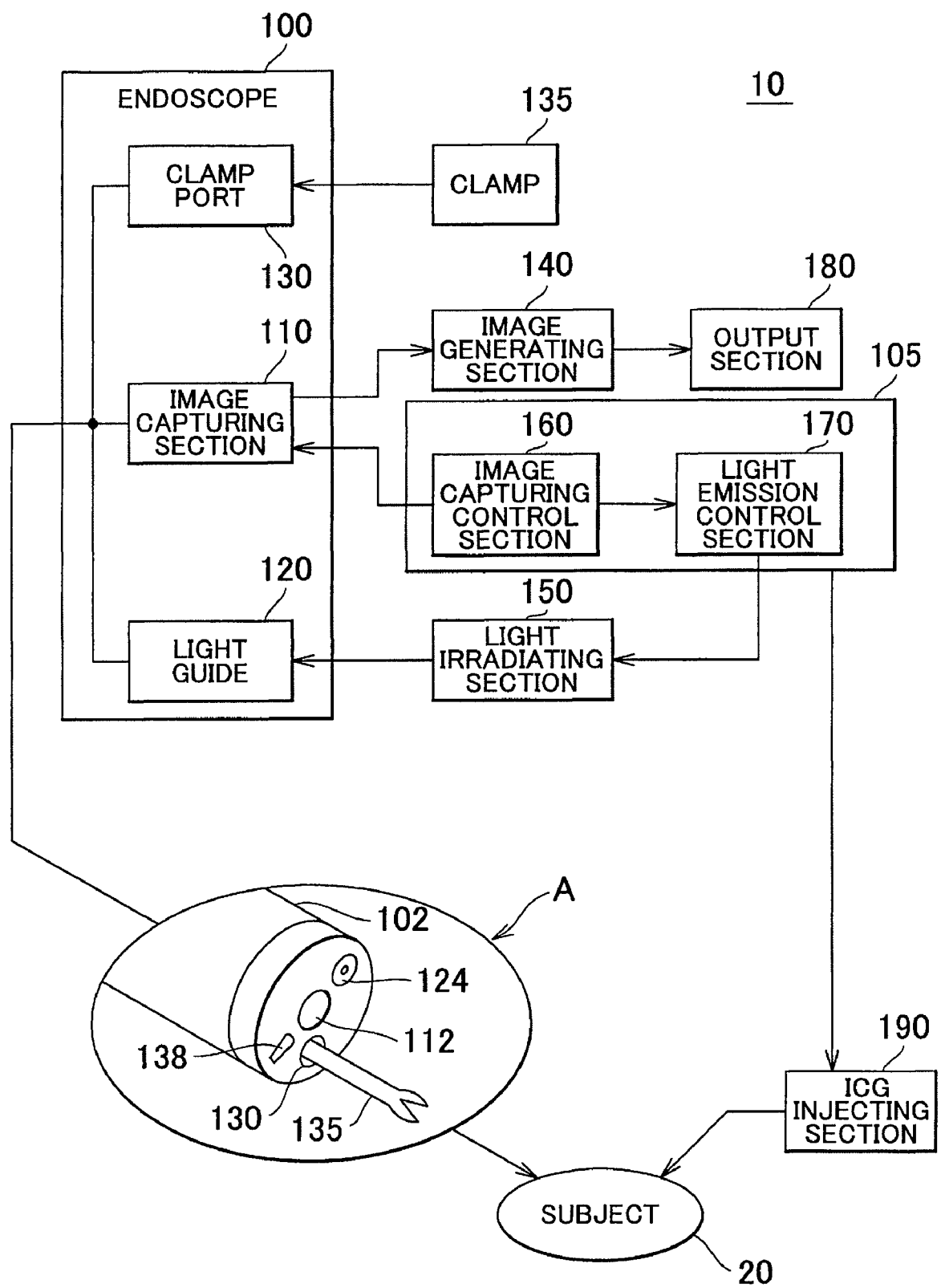
FIG. 1 shows an exemplary configuration of an image capturing system 10 according to the present embodiment, along with a subject 20.

FIG. 1 shows an exemplary configuration of an image capturing system 10 according to the present embodiment, along with a subject 20. The image capturing system 10 is provided with an endoscope 100, an image generating section 140, an output section 180, a control section 105, a light irradiating section 150, and an ICG injecting section 190. In FIG. 1, the section "A" is an enlarged view of the tip 102 of the endoscope 100.

The ICG injecting section 190 injects indocyanine green (ICG), which is a luminescent substance, into the subject 20, which is an example of the image capturing target. The ICG is an example of the luminescent substance in the present embodiment, but the luminescent substance may instead be a different fluorescent substance. The ICG is excited by infrared rays with a wavelength of 750 nm, for example, to emit broad spectrum fluorescence centered at 810 nm.

If the subject 20 is a living organism, the ICG injecting section 190 injects the ICG into the blood vessels of the organism through intravenous injection. The image capturing system 10 captures images of the blood vessels in the organism from the luminescent light of the ICG. This luminescent light is an example of a specified wavelength region, and includes fluorescent light and phosphorescent light. The luminescent light, which is an example of the light from the image capturing target, includes chemical luminescence, frictional luminescence, and thermal luminescence, in addition to the luminescence from the excitation light or the like.

The ICG injecting section 190 is controlled by the control section 105, for example, to inject the subject 20 with ICG such that the ICG density in the organism is held substantially constant. The subject 20 may be a living organism such as a person, and serves as the image capturing target for the image being processed by the image capturing system 10. Objects such as blood vessels exist inside the subject 20.

The endoscope 100 includes an image capturing section 110, a light guide 120, and a clamp port 130. The tip 102 of the endoscope 100 includes an objective lens 112, which is a portion of the image capturing section 110, an irradiation aperture 124, which is a portion of the light guide 120, and a nozzle 138.

A clamp 135 is inserted into the clamp port 130, and the clamp port 130 guides the clamp 135 to the tip 102. The tip of the clamp 135 may be any shape. Instead of the clamp, various types of instruments for treating the organism can be inserted into the clamp port 130. The nozzle 138 ejects water or air.

The light irradiating section 150 generates the light to be radiated from the tip 102 of the endoscope 100. The light generated by the light irradiating section 150 includes irradiation light that irradiates the subject 20 and excitation light, such as infra-red light, that is in a wavelength region that excites the luminescent substance inside the subject 20 such that the luminescent substance emits light in a specified wavelength region. The irradiation light may include a red component, a green component, and a blue component.

The light guide 120 may be formed of optical fiber. The light guide 120 guides the light emitted by the light irradiating section 150 to the tip 102 of the endoscope 100. The light guide 120 can have the irradiation aperture 124 provided in the tip 102. The light emitted by the light irradiating section 150 passes though the irradiation aperture 124 to irradiate the subject 20.

The image capturing section 110 receives at least one of the light generated by the luminescent substance and the light resulting from the irradiation light being reflected by the object. The image generating section 140 generates an image by processing the received-light data acquired from the image capturing section 110. The output section 180 outputs the image generated by the image generating section 140.

The control section 105 includes an image capturing control section 160 and a light emission control section 170. The image capturing control section 160 controls the image capturing performed by the image capturing section 110. The light emission control section 170 controls the light irradiating section 150 based on the control received from the image capturing control section 160. For example, if the image capturing section 110 performs image capturing by alternately using infra-red light and irradiation light including red, green, and blue components, the light emission control section 170 controls the light irradiating the subject 20 from the light irradiating section 150 such that the timing of the irradiation with the irradiation light is synchronized with the timing of the image capturing.

Figure 2:
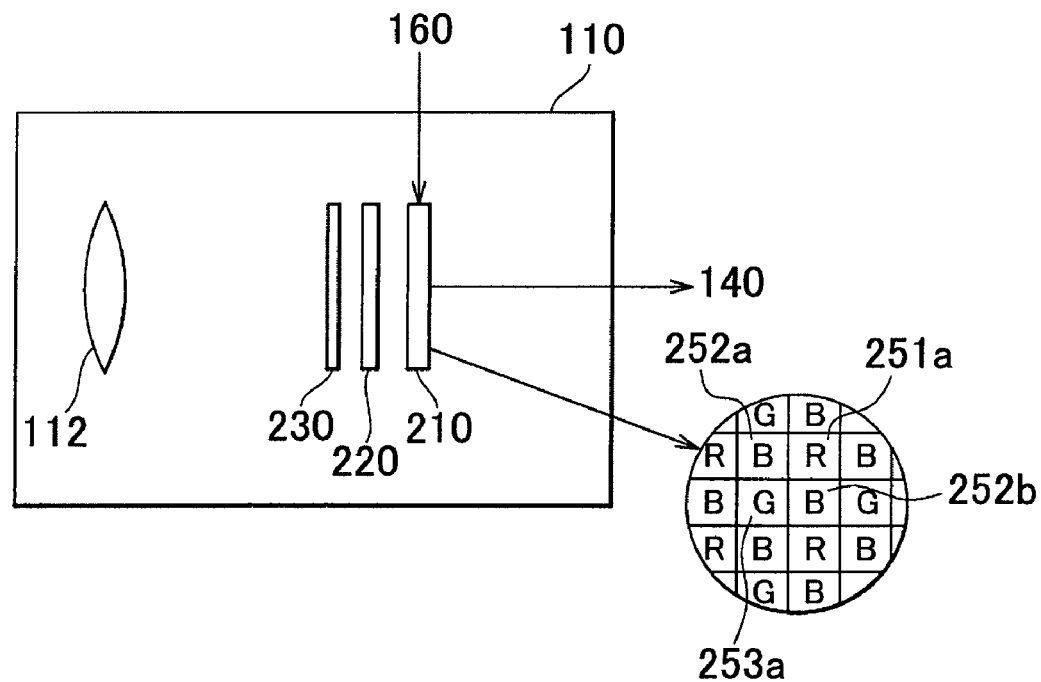
FIG. 2 shows an exemplary configuration of the image capturing section 110.

FIG. 2 shows an exemplary configuration of the image capturing section 110. The image capturing section 110 includes the objective lens 112, an image capturing device 210, a spectral filter section 220, and a lens-side excitation light cut filter 230. The image capturing device 210 includes a plurality of first light receiving elements 251 including a first light receiving element 251a, a plurality of second light receiving elements 252 including a second light receiving element 252a and a second light receiving element 252b, and a plurality of third light receiving elements 253 including a third light receiving element 253a.

The following describes the function and operation of the configurational elements in the image capturing section 110. For the sake of simplicity, the following description refers to a single first light receiving element 251, a single second light receiving element 252, and a single third light receiving element 253. Furthermore, the plurality of first light receiving elements 251, second light receiving elements 252, and third light receiving element 253 may be referred to simply as "the light receiving elements."

The first light receiving element 251, the second light receiving element 252, and the third light receiving element 253 receive light from the subject via the objective lens 112. More specifically, the first light receiving element 251 receives light in a specified wavelength region and light in a first wavelength region, which is different from the specified wavelength region. The second light receiving element 252 receives light in a second wavelength region, which is different from the specified wavelength region. The third light receiving element 253 receives light in a third wavelength region, which is different from the specified wavelength region, the first wavelength region, and the second wavelength region.

The first wavelength region, the second wavelength region, and the third wavelength region are each different wavelength regions that do not overlap with each other. The first light receiving element 251, the second light receiving element 252, and the third light receiving element 253 are arranged 2-dimensionally in a prescribed pattern.

The spectral filter section 220 includes a plurality of filter elements that each allow one of the light in the first wavelength region, the light in the second wavelength region, and the light in the third wavelength region to pass through. The filter elements are arranged 2-dimensionally to correspond respectively to the first light receiving element 251, the second light receiving element 252, and the third light receiving element 253. Each light receiving element receives the light that passes through the corresponding filter element. In this way, the first light receiving element 251, the second light receiving element 252, and the third light receiving element 253 each receive light in a different wavelength region.

The lens-side excitation light cut filter 230 is provided at least between (i) the subject and (ii) the second light receiving element 252 and the third light receiving element 253, and cuts the light in the wavelength region of the excitation light. The second light receiving element 252 and the third light receiving element 253 receive the light reflected by the subject through the lens-side excitation light cut filter 230. Therefore, the second light receiving element 252 and the third light receiving element 253 do not substantially receive the light resulting from the excitation light being reflected by the subject.

The lens-side excitation light cut filter 230 may cut the light in the wavelength region of the excitation light and the light in the specified wavelength region. In this case, the second light receiving element 252 and the third light receiving element 253 do not substantially receive the luminescent light from the subject, for example.

The lens-side excitation light cut filter 230 may be provided between the subject and the first light receiving element 251. In this case, the lens-side excitation light cut filter 230 allows the luminescent light to pass through.

In the same manner as the spectral filter section 220, the lens-side excitation light cut filter 230 may include filter elements that are arranged 2-dimensionally corresponding respectively to the first light receiving element 251, the second light receiving element 252, and the third light receiving element 253. The filter element supplying light to the first light receiving element 251 allows at least light in the first wavelength region and light in the specified wavelength region to pass through. The filter element supplying light to the first light receiving element 251 may cut the light in the wavelength region of the excitation light. The filter element supplying light to the second light receiving element 252 cuts the light in the wavelength region of the excitation light and the light in the specified wavelength region, and allows at least the light in the second wavelength region to pass through. The filter element supplying light to the third light receiving element 253 cuts the light in the wavelength region of the excitation light and the light in the specified wavelength region, and allows at least the light in the third wavelength region to pass through.

The image generating section 140 determines the pixel value for a single pixel based on at least the amount of light received by the first light receiving element 251a, the second light receiving element 252a, the second light receiving element 252b, and the third light receiving element 253a. In other words, the first light receiving element 251a, the second light receiving element 252a, the second light receiving element 252b, and the third light receiving element 253a are arranged 2-dimensionally to form a single pixel element, and a plurality of pixel elements are formed by 2-dimensionally arranging a plurality of such groups of light receiving elements forming a single pixel element. The light receiving elements are not limited to the arrangement shown in FIG. 2, and may instead be arranged in a variety of different arrangements.

Figure 3:
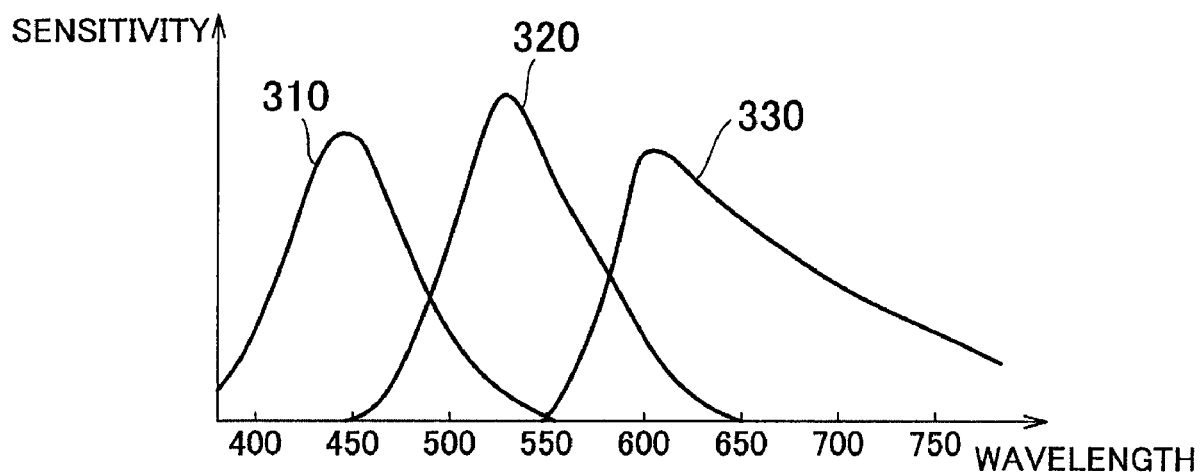
FIG. 3 shows exemplary spectral sensitivity characteristics of the first light receiving element 251, the second light receiving element 252, and the third light receiving element 253.

FIG. 3 shows exemplary spectral sensitivity characteristics of the first light receiving element 251, the second light receiving element 252, and the third light receiving element 253. The line 330, the line 310, and the line 320 represent the spectral sensitivity distributions of the first light receiving element 251, the second light receiving element 252, and the third light receiving element 253, respectively. For example, the first light receiving element 251 is sensitive to light having a wavelength around 650 nm, and the other light receiving elements are not substantially sensitive to this light. The second light receiving element 252 is sensitive to light having a wavelength around 450 nm, and the other light receiving elements are not substantially sensitive to this light. The third light receiving element 253 is sensitive to light having a wavelength around 550 nm, and the other light receiving elements are not substantially sensitive to this light.

The first light receiving element 251 can receive the light in the infra-red spectrum, i.e. 810 nm, which is an example of the specified wavelength region. This spectral sensitivity characteristic depends on the transmission characteristics of the lens-side excitation light cut filter 230 and the spectral filter section 220 and the spectral sensitivity of each light receiving element.

In this way, the first light receiving element 251, the second light receiving element 252, and the third light receiving element 253 receive the red component, the green component, and the blue component of light, respectively. The first light receiving element 251 can also receive the light in the infra-red spectrum, which is an example of the specified wavelength region. The first light receiving element 251, the second light receiving element 252, and the third light receiving element 253 may be image capturing elements such as CCDs, CMOSs, or the like. The spectral sensitivity characteristics of the first light receiving element 251, the second light receiving element 252, and the third light receiving element 253, as represented by the line 330, the line 310, and the line 320, are obtained by a combination of the spectral transmission factor of the lens-side excitation light cut filter 230, the spectral transmission factors of the filter elements in the spectral filter section 220, and the spectral sensitivity of the image capturing elements themselves.

Figure 4:
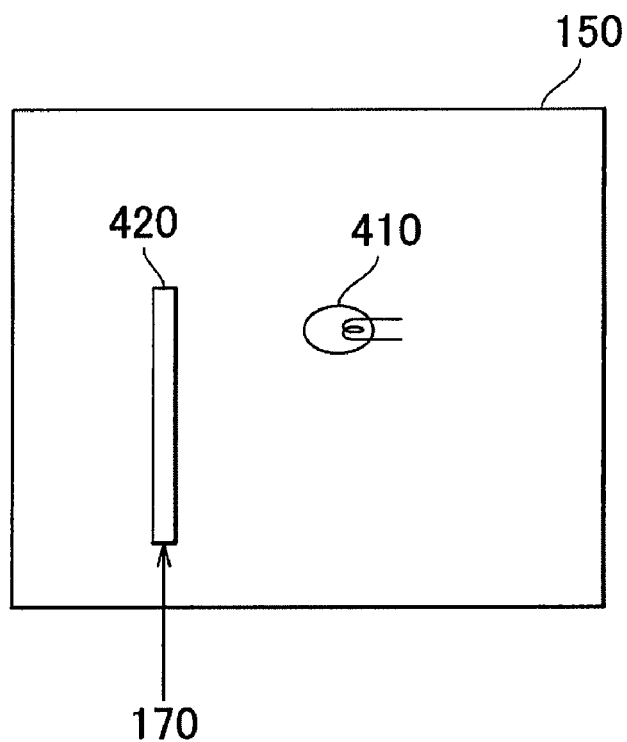
FIG. 4 shows an exemplary configuration of the light irradiating section 150.

FIG. 4 shows an exemplary configuration of the light irradiating section 150. The light irradiating section 150 includes a light emitting section 410 and a light source filter section 420. The light emitting section 410 emits light in a wavelength region that includes the wavelength region of the excitation light, the first wavelength region, the second wavelength region, and the third wavelength region. The light emitting section 410 of the present embodiment may be a xenon lamp.

Figure 5:
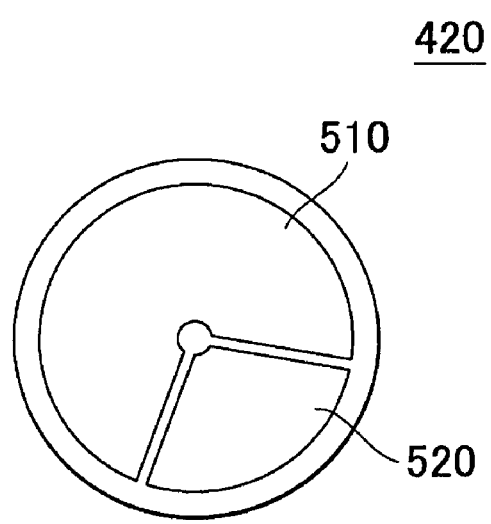
FIG. 5 shows an exemplary configuration of the light source filter section 420.

FIG. 5 shows an exemplary configuration of the light source filter section 420 as seen from the direction in which the light is guided from the light emitting section 410. The light source filter section 420 includes an irradiation light cut filter section 520 and an excitation light cut filter section 510. The light emission control section 170 rotates the light source filter section 420 in a plane substantially perpendicular to the direction in which the light emitted by the light emitting section 410 travels, with the central axis of the light source filter section 420 serving as the center of rotation.

The excitation light cut filter section 510 cuts the light in the wavelength region of the excitation light, and allows the light in the first wavelength region, the light in the second wavelength region, and the light in the third wavelength region to pass through. The irradiation light cut filter section 520 allows the light in the wavelength region of the excitation light, the light in the second wavelength region, and the light in the third wavelength region to pass through. The irradiation light cut filter section 520 desirably cuts the light in the first wavelength region. The light from the light emitting section 410 is guided to a position shifted from the central axis of the light source filter section 420.

Accordingly, when the light from the light emitting section 410 is guided to the excitation light cut filter section 510, the excitation light cut filter section 510 cuts the light in the wavelength region of the excitation light and allows the light in the first wavelength region, the light in the second wavelength region, and the light in the third wavelength region to pass through. Therefore, at this time, the subject is irradiated with the light in the first wavelength region, the light in the second wavelength region, and the light in the third wavelength region.

On the other hand, when the light from the light emitting section 410 is guided to the irradiation light cut filter section 520, the light in the wavelength region of the excitation light, the light in the second wavelength region, and the light in the third wavelength region are allowed to pass through the irradiation light cut filter section 520. Therefore, at this time, the subject is irradiated with the excitation light, the light in the second wavelength region, and the light in the third wavelength region.

The image capturing section 110 is controlled by the image capturing control section 160 to receive the visible light reflected by the subject 20 while the visible light is being emitted, where the visible light is the light in the first wavelength region, the light in the second wavelength region, and the light in the third wavelength region. The image generating section 140 generates the visible light image based on the amount of light received by the image capturing section 110.

Furthermore, the image capturing section 110 is controlled by the image capturing control section 160 to receive the luminescent light emitted by the ICG inside the subject, the light in the second wavelength region reflected by the subject 20, and the light in the third wavelength region reflected by the subject 20, while the excitation light, the second wavelength region, and the third wavelength region are being emitted. The image generating section 140 generates the luminescent light image based on the amount of luminescent light received by the image capturing section 110, and generates the visible light image based on the amount of light received in the second and third wavelength regions, and the amount of light in the first wavelength region received by the image capturing section 110 at another timing.

Figure 6:
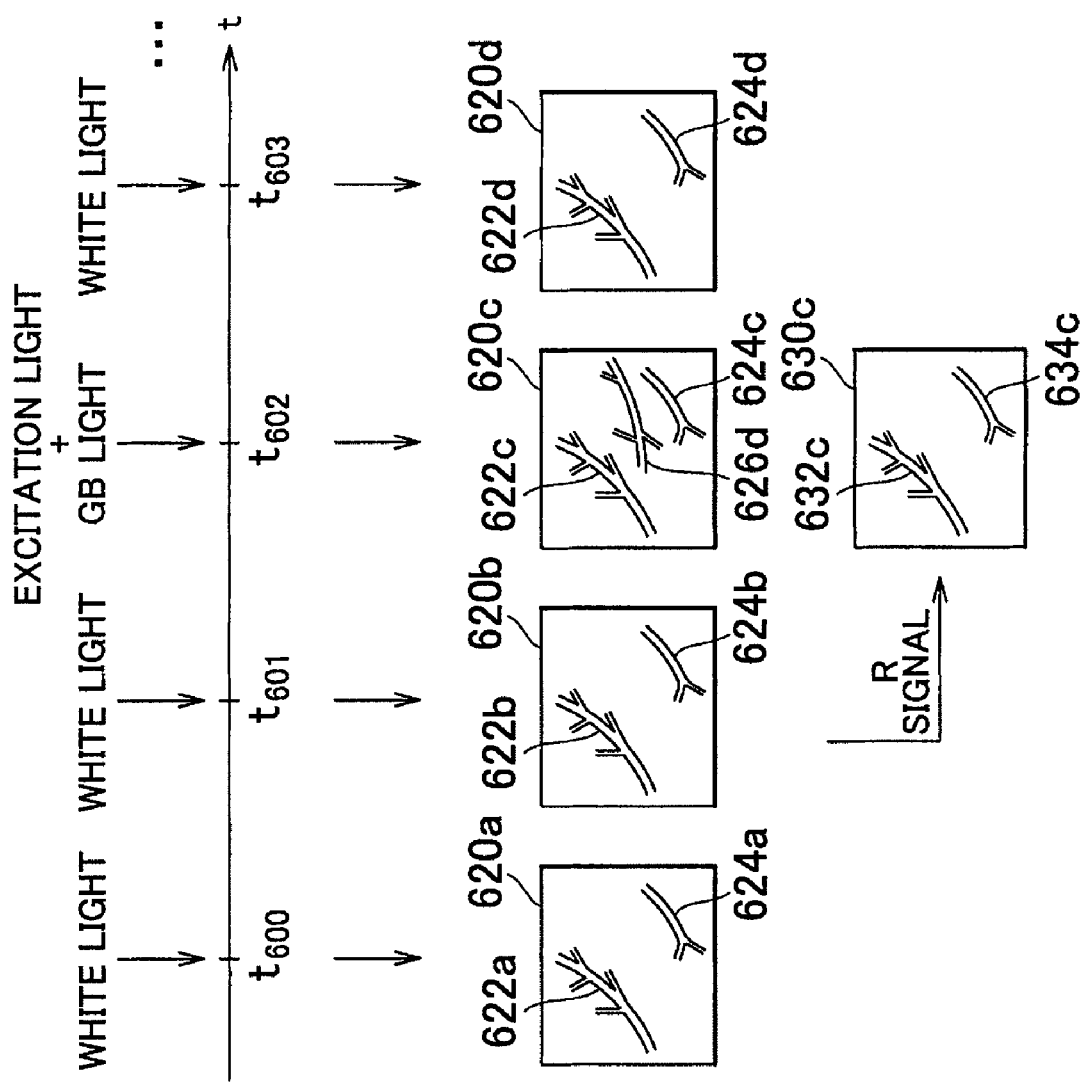
FIG. 6 shows the timing of the image capturing by the image capturing section 110 and exemplary images generated by the image generating section 140.

FIG. 6 shows the timing of the image capturing by the image capturing section 110 and exemplary images generated by the image generating section 140. The image capturing control section 160 causes the image capturing section 110 to capture images based on the light from the object at times t600, t601, t602, t603, etc. The light emission control section 170 is controlled by the image capturing control section 160 to irradiate the subject with the light emitted by the light emitting section 410 through the excitation light cut filter section 510, at first timings that include t600, t601, and t603. In this way, the light emission control section 170 irradiates the subject with light in a wavelength region including the first wavelength region, the second wavelength region, and the third wavelength region at the first timings.

At the first timings, the image capturing control section 160 irradiates the subject with light in a wavelength region including the first wavelength region, the second wavelength region, and the third wavelength region. The image capturing control section 160 separates the light reflected from the object such that the first light receiving element 251 receives the light in the first wavelength region, the second light receiving element 252 receives the light in the second wavelength region, and the third light receiving element 253 receives the light in the third wavelength region. In this way, the image capturing control section 160 causes the first light receiving element 251 to receive the light in the first wavelength region, causes the second light receiving element 252 to receive the light in the second wavelength region, and causes the third light receiving element 253 to receive the light in the third wavelength region, at the first timings.

At second timings, which include t602, the image capturing control section 160 controls the light emission control section 170 to irradiate the subject with the light emitted by the light emitting section 410 through the irradiation light cut filter section 520. In this way, the light emission control section 170 irradiates the subject with the excitation light and the light in the wavelength region including the second wavelength region and the third wavelength region at the second timings.

The image capturing control section 160 causes the first light receiving element 251 to receive light in the specified wavelength region emitted from the subject at the second timings. In other words, the image capturing control section 160 causes the first light receiving element 251 to receive the light in the specified wavelength region from the subject at the second timings.

In this way, the control section 105 irradiates the subject with the excitation light, the light in the second wavelength region, and the light in the third wavelength region at the second timings, but does not irradiate the subject with the light in the first wavelength region. At this time, the first light receiving element 251 receives the light in the specified wavelength region emitted by the subject, the second light receiving element 252 receives the light in the second wavelength region reflected from the subject, and the third light receiving element 253 receives the light in the third wavelength region reflected from the subject. The wavelength region of the excitation light is different from the first wavelength region, the second wavelength region, and the third wavelength region, and has a wavelength region that does not overlap with the first wavelength region, the second wavelength region, or the third wavelength region.

As described above, the control section 105 controls the wavelength region of the light received by the first light receiving element 251, the second light receiving element 252, and the third light receiving element 253. The image generating section 140 generates the image of the subject based on the amount of light received by the light receiving elements at the plurality of timings.

The image generating section 140 generates a visible light image 620a, a visible light image 620b, and a visible light image 620d based on the amount of light received by the light receiving elements at the first timings represented by t600, t601, and t603, respectively. The visible light image 620a includes a blood vessel image 622a and a blood vessel image 624a, the visible light image 620b includes a blood vessel image 622b and a blood vessel image 624b, and the visible light image 620d includes a blood vessel image 622d and a blood vessel image 624d.

The visible light image 620a, the visible light image 620b, and the visible light image 620d include surface images showing a physical surface in addition to the blood vessel images. The image generating section 140 generates a subject image at each first timing based on the light in the first wavelength region received by the first light receiving element 251 at the first timing, the light in the second wavelength region received by the second light receiving element 252 at the first timing, and the light in the third wavelength region received by the third light receiving element 253 at the first timing.

The image generating section 140 generates a luminescent light image 620c, which includes a blood vessel image 622c, a blood vessel image 624c, and a blood vessel image 626c, based on the light received by the light receiving elements at the second timings, represented by t602. The image generating section 140 also generates a visible light image 630c based on the amount of light received by the first light receiving element 251 at a first timing, e.g. t601, and the amount of light received by the second light receiving element 252 and the third light receiving element 253 at a second timing, e.g. t602.

In this way, the image generating section 140 generates a subject image at the second timing, based on light in the second wavelength region received by the second light receiving element 252 at the second timing and light in the first wavelength region received by the first light receiving element 251 at the first timing. Accordingly, the image generating section 140 can generate a visible light image even at the timing at which the luminescent light image is captured. The output section 180 displays the visible light images 620a, 620b, 630c, 620d, etc. in series, thereby providing a video without missing frames.

If the subject 20 is a living organism having red blood like a person, the spatial frequency component of the red component in the visible light image is most likely smaller than the spatial frequencies of the green and blue components. Therefore, the amount of degradation of the video due to the red component frames being dropped is likely less than the amount of degradation due to green and blue component frames being dropped. Therefore, the choppy appearance of the video can be decreased more by dropping the red component than by dropping the green and blue components. Accordingly, the image capturing system 10 can provide a visible light video without noticeable frame dropping.

As described above, the image capturing system 10 can capture the luminescent light image 620c based on the luminescent light in the infra-red spectrum emitted by the subject 20 in response to the excitation light in the infra-red spectrum. Excitation light having a wavelength longer than visible light is more difficult to absorb than visible light, and therefore such excitation light penetrates more deeply, e.g. to a depth of approximately 1 cm, to cause the luminescent light to be emitted by the subject 20. Since the luminescent light has a longer wavelength than the excitation light, it is relatively easy for the luminescent light to reach the physical surface. Therefore, the image capturing system 10 can achieve the luminescent light image 620c that includes the blood vessel image 626d deep in the subject, which is not included in the visible light images 620a, 620b, and 620d.

The output section 180 may generate a composite image obtained by combining the luminescent light image 620c with the visible light image 620b or the visible light image 620d that are captured at timings near the timing at which the luminescent light image 620c is captured. The output section 180 then outputs this composite image. The output section 180 may store the luminescent light image 620c in association with the visible light image 620b or the visible light image 620d.

The control section 105 cuts the light in the wavelength region of the excitation light and the light in the wavelength region of the luminescent light out of the light from the light emitting section 410 at the timings at which the visible light images are captured. In this way, the image capturing system 10 can provide an image of the physical surface for observation, without including the blood vessel images inside the subject in the visible light image.

Figure 7:
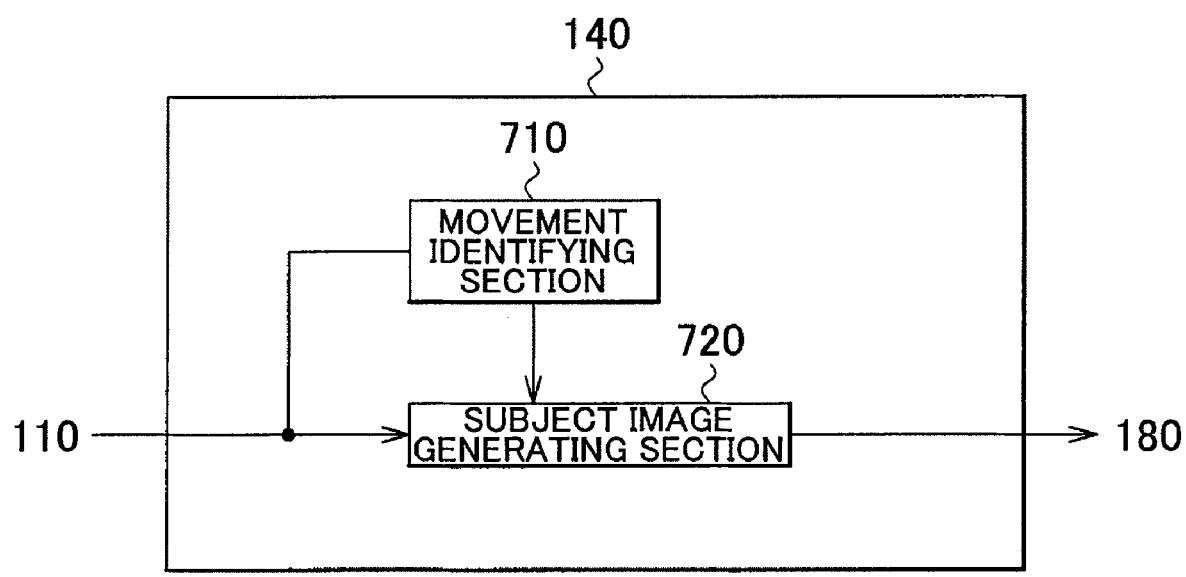
FIG. 7 shows a block configuration of the image generating section 140.

FIG. 7 shows a block configuration of the image generating section 140. For ease of explanation, FIG. 6 is used to describe an exemplary process of generating the visible light image 630c by multiplexing an R signal corresponding to the amount of light received by the first light receiving element 251 at the time t601 with a B signal and a G signal corresponding respectively to the amount of light received by the second light receiving element 252 and the third light emitting element 253 at the time t602. In the following description, the movement of the tip 102 of the endoscope 100, the movement of the subject 20, and the like do not cause a change over time in the image. In this process, the R signal might be skewed in relation to other color signals in the visible light image due to movement of the tip 102 of the endoscope 100, movement of the subject 20, or the like.

FIG. 6 is used to describe the configuration of the image generating section 140 and the operation and function of the image generating section 140 for correcting the effect the movement mentioned above on the visible light image. The image generating section 140 includes a movement identifying section 710 and a subject image generating section 720.

The movement identifying section 710 identifies movement of an object in an image, based on an image created by B signals at a plurality of timings. Here, the movement of an object refers to any movement that causes a change over time in the image, such as movement of the subject 20, movement of the tip 102 of the endoscope 100, or a change over time of the zoom of the image capturing section 110. The movement of the tip 102 of the endoscope 100 includes a change over time of the position of the tip 102 causing the position of the image captured by the image capturing section 110 to change over time, and a change over time of the orientation of the tip 102 that causes the direction in which the image capturing section 110 captures the image to change over time.

The movement identifying section 710 identifies the movement of an object based on the image of the B signal at the times t601 and t602. For example, the movement identifying section 710 identifies the movement of the object by matching the objects extracted from a plurality of images.

The subject image generating section 720 corrects the R signal at the time t601 based on the identified movement, and generates the R signal that is expected for the time t602. The subject image generating section 720 multiplexes the R signal generated through the above correction, the B signal at the time t602, and the G signal at the time t602, to generate the subject image at time t602.

Figure 8:
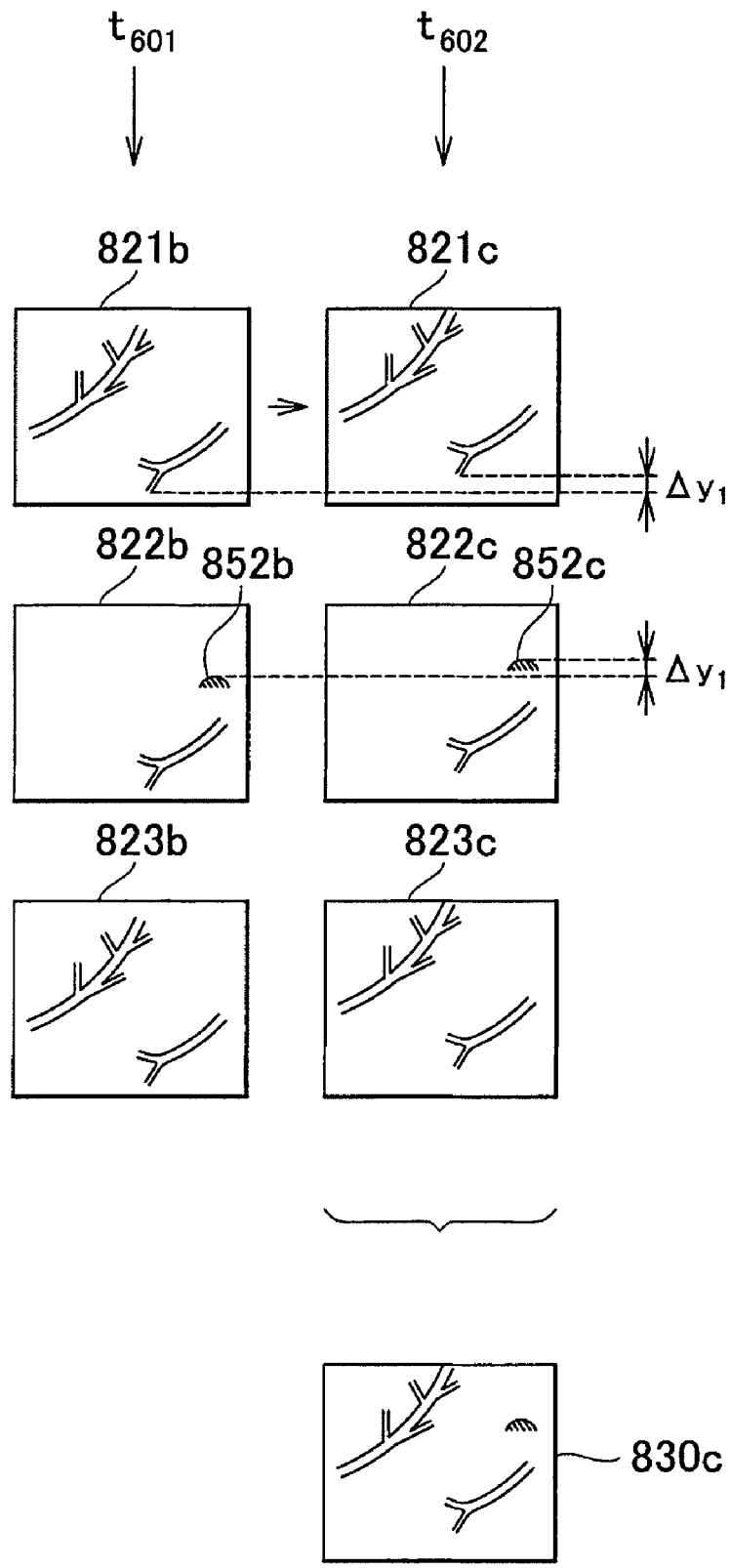
FIG. 8 shows the generation of a subject image in which the movement is corrected.

FIG. 8 shows the generation of a subject image in which the movement is corrected. The image 821b is the image of the R signal from the first light receiving element 251 at the time t601. The image 822b and the image 822c are images of the B signal from the second light receiving element 252 at the times t601 and t602, respectively. The image 823b and the image 823c are images of the G signal from the third light receiving element 253 at the times t601 and t602, respectively.

Here, the movement identifying section 710 identifies the movement based on the content of the image 822b and the image 822c. More specifically, the movement identifying section 710 extracts objects from the image 822b and the image 822c that show the same subject. In the present embodiment, the movement identifying section 710 extracts the objects 852b and 852c from the image 822b and the image 822c, respectively.

The movement identifying section 710 calculates the difference in position between the object 852b and the object 852c. In FIG. 8, for ease of explanation, the position difference exists in the y-direction of the image so that the movement identifying section 710 calculates a positional difference Δy1 indicating the positional difference between the object 852b and the object 852c.

The subject image generating section 720 generates the image 821c by shifting the image 821b in the y-direction by an amount corresponding to the calculated positional difference Δy1. The subject image generating section 720 generates the subject image 830c by combining the image 821c, the image 822c, and the image 823c. Here, combining the images includes a process for multiplexing the R signal showing the image 821c, the B signal showing the image 822c, and the G signal showing the image 823c, with a prescribed weighting.

The above describes an example in which the movement is identified using the image 822 of the B signal, but the movement can be identified in the same manner using the image 823 of the G signal. The decision concerning which image's waveform the movement identifying section 710 uses to identify the movement can be decided based on the contrast of the captured image. For example, the movement identifying section 710 can prioritize the use of the image having the highest contrast for identifying the movement. If an object with a minute structure is used as the object for identifying the movement, i.e. it is clear that the object has a very fine surface structure, using the image of the B signal might enable more accurate movement identification. If an object with an uneven structure is used for identifying the movement, i.e. it is clear that the object has a bumpy surface structure, using the image of the G signal might enable more accurate movement identification.

The subject image generating section 720 may change the movement correction amount for each image region in the image of the R signal. For example, if the image capturing direction of the image capturing section 110 is perpendicular to the surface of the subject and the tip 102 of the endoscope 100 moves horizontally in relation to the surface of the subject, the movement amount of the object is the same in every image region. On the other hand, if the image capturing direction of the image capturing section 110 is not perpendicular to the surface of the subject, for example, the movement amount in image regions captured at positions further from the tip 102 might be smaller than the movement amount in image regions captured at positions closer to the tip 102.

In order to calculate the movement correction amount for each image region in the image of the R signal, the subject image generating section 720 can calculate the movement correction amount based on the position of an image region and a positional relationship between the surface of the subject and the image capturing section 110, if this positional relationship is known in advance or can be estimated. The subject image generating section 720 may calculate the movement correction amount for the image of the R signal based on a control value that manipulates the endoscope 100 to cause a change over time in the image. The control value may be a value that controls the position or orientation of the tip 102, a value that controls the zoom of the image capturing section 110, or the like.

As another example, the movement identifying section 710 may calculate the movement of the object in each image region. The subject image generating section 720 may calculate the movement correction amount for each image region in the image based on the movement of an object in each image region.

When identifying the movement in each image region, the movement identifying section 710 may determine which wavelength image is used to identify the movement in each image region. For example, the movement identifying section 710 calculates the contrast of each image region in each image. The movement identifying section 710 may then give priority to selecting the image of the wavelength for which the highest contrast was calculated and uses this image for the corresponding image region. The movement identifying section 710 uses the plurality of selected waveforms to identify the movement of the objects.

As described in relation to FIGS. 7 and 8, the movement identifying section 710 identifies the amount of movement of an object between an image at the first timing and an image at the second timing, based on the image resulting from the light in the second wavelength region received by the second light receiving element 252 at the first timing and the image resulting from the light in the second wavelength region received by the second light receiving element 252 at the second timing. The subject image generating section 720 generates the subject image at the second timing based on the light in the first wavelength region received by the first light receiving element 251 at the first timing, the light in the second wavelength region received by the second light receiving element 252 at the second timing, and the movement of the object.

Figure 9:
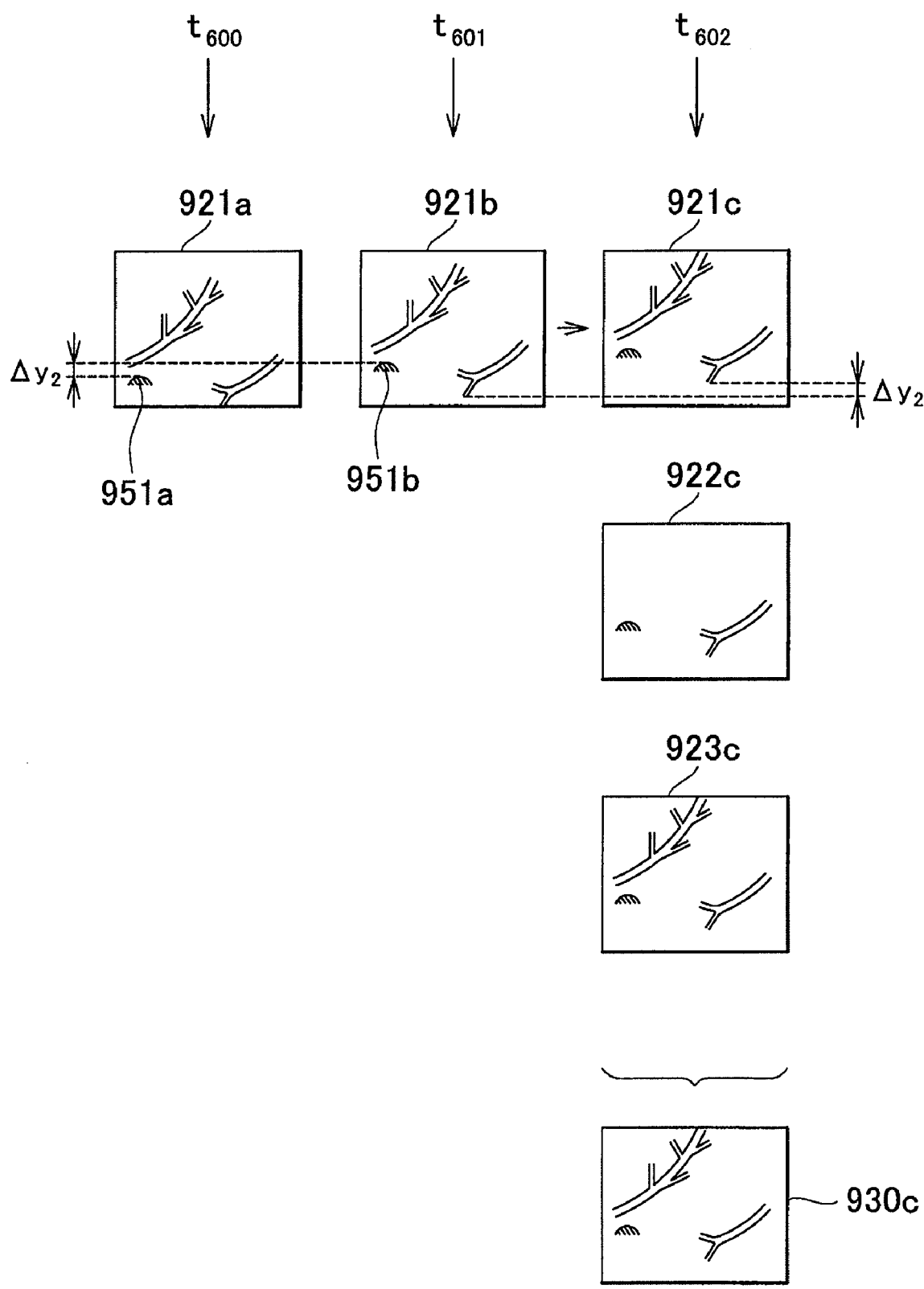
FIG. 9 shows another example of the generation of a subject image in which the movement is corrected.

FIG. 9 shows another example of the generation of a subject image in which the movement is corrected. In the examples in FIG. 9, the movement identifying section 710 identifies the movement using the image 921a of the R signal obtained at the time t600 and the image 921b of the R signal obtained at the time t601. In the same manner as the method described in relation to FIG. 8, the movement identifying section 710 extracts objects that indicate the same subject in the image 921a and the image 921b. In FIG. 9, the movement identifying section 710 extracts the object 951a and the object 951b from the image 921a and the image 921b, respectively.

The movement identifying section 710 calculates the positional difference between the object 951a and the object 951b. In FIG. 9, for ease of explanation, the position difference exists in the y-direction of the image so that the movement identifying section 710 calculates the positional difference Δy2 indicating the positional difference between the object 951a and the object 951b. In the same manner as described in relation to FIG. 8, the subject image generating section 720 generates the image 921c by shifting the image 921b in the y-direction by an amount corresponding to the calculated positional difference Δy2.

The above example uses the image 921a and the image 921b to identify the movement, but the movement identifying section 710 may instead identify the movement using the image 921b and the image of the R signal obtained at the time t603. In this way, the movement identifying section 710 may identify the movement based on the images obtained at a plurality of timings before and after the time t601, which is the timing at which the image of the R signal in which the movement is corrected is generated. If it is acceptable for the display of the visible light image to be somewhat delayed, the movement identifying section 710 can more accurately identify the movement by also using images at later timings.

As described in relation to FIG. 9 the movement identifying section 710 identifies the movement of the objects between images obtained at a plurality of timings, based on a plurality of images resulting from the light in the first wavelength region received by the first light receiving element 251 at a plurality of timings that include the first timings but not the second timing. The subject image generating section 720 generates the subject image at the second timing based on the light in the first wavelength region received by the first light receiving element 251 at the first timings, the light in the second wavelength region received by the second light receiving element 252 at the second timing, and the movement of the object.

FIGS. 8 and 9 are used to described examples of the movement identification processes in which the movement is identified using images captured by the movement identifying section 710 at the second timing, but the movement identifying section 710 may instead identify the movement using images captured at three or more timings. The movement identifying section 710 can select an image for identifying the movement for each image region, from among the images of the R signal in addition to the images of the B signal and the images of the G signal.

Figure 10:
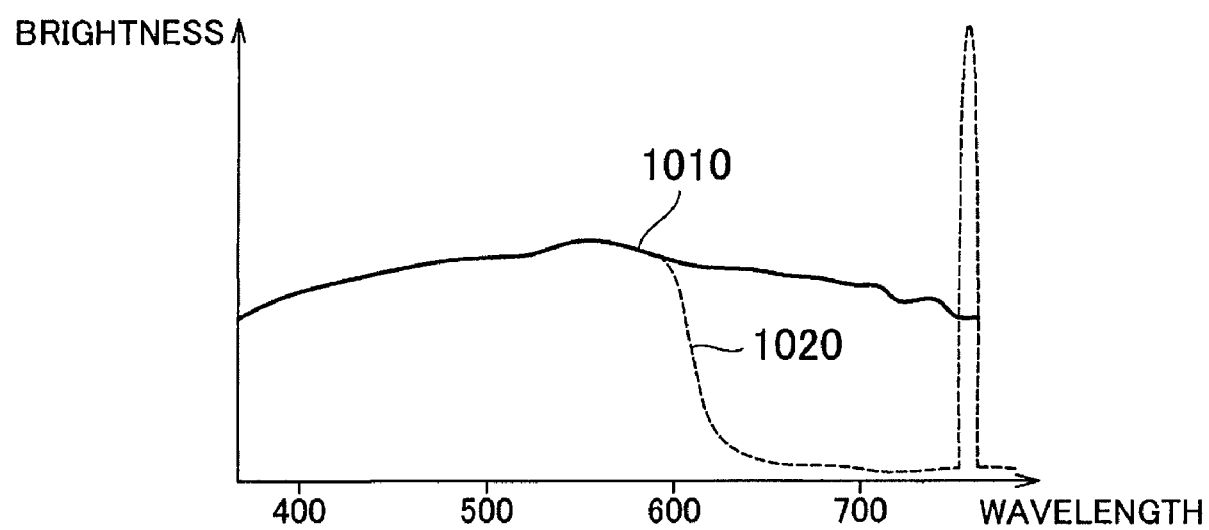
FIG. 10 shows an exemplary spectrum of the light irradiating the subject.

FIG. 10 shows an exemplary spectrum of the light irradiating the subject. The line 1010 represents the spectrum of substantially white light, which irradiates the subject at the first timings t600, t601, and t603, as described in FIG. 6.

The line 1020 represents the spectrum of the light irradiating the subject at the second timing t602 described in FIG. 6. As shown by this spectrum, the irradiation light may have a substantial spectral intensity in the first wavelength region at the second timing. The spectrum of the irradiation light at the first timings and the spectrum of the irradiation light at the second timing are different in the specified wavelength region, which is the wavelength region of the excitation light. As shown in FIG. 10, the light irradiating section 150 may radiate light that in which a ratio of the spectral intensity of the specified wavelength region to the spectral intensity of the first wavelength region changes such that this ratio is larger at the second timing than at the first timings. More specifically, the light irradiating section 150 radiates light at the first timings in which the spectral intensity of the first wavelength region is greater than the spectral intensity of the specified wavelength region, and radiates light at the second timing in which the spectral intensity of the specified wavelength region is greater than the spectral intensity of the first wavelength region.

FIGS. 4 and 5 describe an embodiment in which the irradiation light cut filter section 520 cuts the light in the first wavelength region, but the irradiation light cut filter section 520 need not completely cut the light in the first wavelength region. Even if the light having a spectral intensity in the first wavelength region is radiated at the second timing, an image of the specified wavelength region can be obtained at the second timing as long as the irradiation light has a spectral intensity in the specified wavelength region sufficient for achieving a clear luminescence image.

As described in relation to FIG. 10, the control section 105 controls the spectrum of the light received by the first light receiving element 251. More specifically, at the first timings, the control section causes the first light receiving element 251 to receive light in a wavelength region that includes the first wavelength region reflected by the subject, and causes the second light receiving element 252 to receive the light in the second wavelength region. At the second timing, the control section 105 causes the first light receiving element 251 to receive light in a wavelength region that includes the specified wavelength region reflected by the subject, and causes the second light receiving element 252 to receive the light in the second wavelength region. Here, the light in the wavelength region that includes the first wavelength region from the subject may be light that includes mainly light in the first wavelength region. The light in the wavelength region that includes the specified wavelength region may be light that includes mainly light in the specified wavelength region.

FIGS. 4 and 5 are used to describe an operation of the light irradiating section 150 that involves controlling the spectrum of the irradiation light from the light emitting section 410 over time by rotating the light source filter section 420. As another example, the light irradiating section 150 need not include the light source filter section 420. More specifically, the light emitting section 410 may include a plurality of light emitting elements that each emit light in a different spectrum. In this case, the control section 105 may control the spectrum of the light irradiating the subject at the first timings and the second timing by controlling the spectral intensity of each light emitting element.

For example, the light emitting section 410 may include a light emitting element that emits light in the red wavelength region, a light emitting element that emits light in the blue wavelength region, a light emitting element that emits light in the green wavelength region, and a light emitting element that emits light in the excitation light wavelength region. Semiconductor elements such as LEDs may be used as the light emitting elements that emit visible light. A semiconductor element such as a semiconductor laser may be used as the light emitting element that emits the excitation light. The light emitting elements may instead be fluorescent bodies that emit luminescent light such as fluorescence when excited.

The control section 105 can control the spectrum of the light irradiating the subject by controlling the emission intensity of each light emitting element at each timing. Here, "controlling the emission intensity of each light emitting element" involves changing the combination of light emitting elements that emit light at each timing. Each light emitting element may include a light emitting body and a filter that allows selected light in a specified wavelength region to pass through. Any type of light emitting elements can be used as the plurality of light emitting elements that each emit light in a different spectrum, as long as the light that has been emitted from the light emitting body and has passed through the filter results in light in different spectrums.

The light emitting elements may be provided on the tip 102 of the endoscope 100. The light emitting elements may emit light in response to electric excitation, or may emit light in response to optical excitation. If the light irradiating section 150 includes light emitting elements emit light in response to optical excitation, the light irradiating section 150 also includes an exciting section that emits light for exciting the light emitting elements. These light emitting elements may emit light in different spectrums according to the wavelength of the light used for excitation. In this case, the control section 105 can control the spectrum of the irradiation light by controlling the wavelength of the light used for excitation emitted by the light emitting section at each timing. As another example, the spectrum of the light emitted by each light emitting element in response to the light used for excitation may be different for each light emitting element. As yet another example, light used for excitation that has passed through the light emitting elements may serve as the irradiation light for irradiating the subject.

By applying the image capturing system 10 described above to an actual system, when a doctor or the like performs surgery while watching the video displayed by the output section 180, the doctor can observe internal blood vessels that cannot be seen at the surface. Furthermore, the image capturing system 10 described above enables the doctor to perform surgery while watching visible light images that do not have dropped frames.

Figure 11:
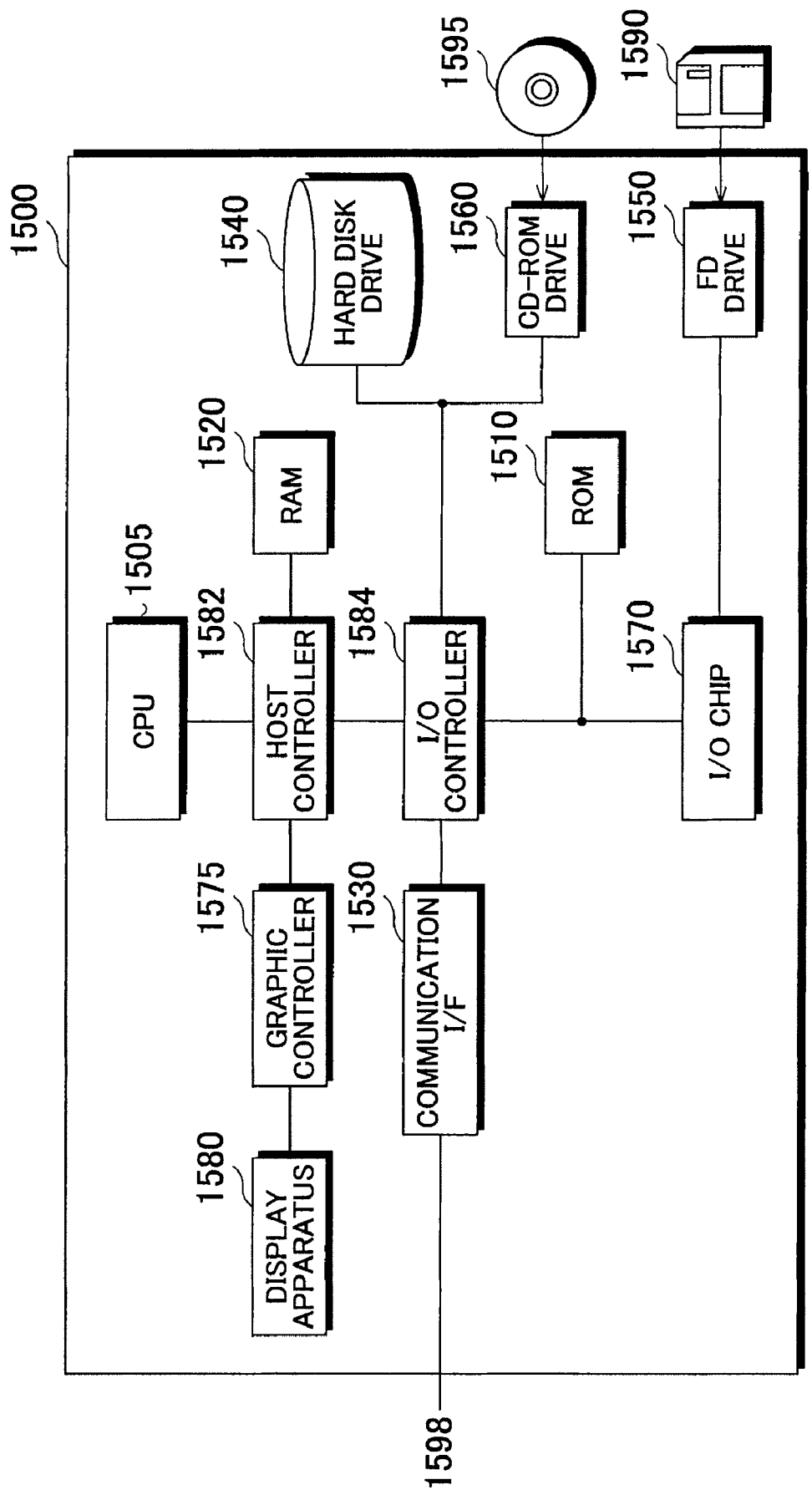
FIG. 11 shows an exemplary hardware configuration of a computer 1500 functioning as the image capturing system 10.

FIG. 11 shows an exemplary hardware configuration of a computer 1500 functioning as the image capturing system 10. The image capturing system 10 according to the present embodiment is provided with a CPU peripheral section that includes a CPU 1505, a RAM 1520, a graphic controller 1575, and a display apparatus 1580 connected to each other by a host controller 1582; an input/output section that includes a communication interface 1530, a hard disk drive 1540, and a CD-ROM drive 1560, all of which are connected to the host controller 1582 by an input/output controller 1584; and a legacy input/output section that includes a ROM 1510, a flexible disk drive 1550, and an input/output chip 1570, all of which are connected to the input/output controller 1584.

The host controller 1582 is connected to the RAM 1520 and is also connected to the CPU 1505 and graphic controller 1575 accessing the RAM 1520 at a high transfer rate. The CPU 1505 operates to control each section based on programs stored in the ROM 1510 and the RAM 1520. The graphic controller 1575 acquires image data generated by the CPU 1505 or the like on a frame buffer disposed inside the RAM 1520 and displays the image data in the display apparatus 1580. In addition, the graphic controller 1575 may internally include the frame buffer storing the image data generated by the CPU 1505 or the like.

The input/output controller 1584 connects the hard disk drive 1540, the communication interface 1530 serving as a relatively high speed input/output apparatus, and the CD-ROM drive 1560 to the host controller 1582. The communication interface 1530 communicates with other apparatuses via the network. The hard disk drive 1540 stores the programs used by the CPU 1505 in the image capturing system 10. The CD-ROM drive 1560 reads the programs and data from a CD-ROM 1595 and provides the read information to the hard disk drive 1540 via the RAM 1520.

Furthermore, the input/output controller 1584 is connected to the ROM 1510, and is also connected to the flexible disk drive 1550 and the input/output chip 1570 serving as a relatively high speed input/output apparatus. The ROM 1510 stores a boot program performed when the image capturing system 10 starts up, a program relying on the hardware of the image capturing system 10, and the like. The flexible disk drive 1550 reads programs or data from a flexible disk 1590 and supplies the read information to the hard disk drive 1540 and via the RAM 1520. The input/output chip 1570 connects the flexible disk drive 1550 to each of the input/output apparatuses via, for example, a parallel port, a serial port, a keyboard port, a mouse port, or the like.

The programs provided to the hard disk drive 1540 via the RAM 1520 are stored on a recording medium such as the flexible disk 1590, the CD-ROM 1595, or an IC card and are provided by the user. The programs are read from the recording medium, installed on the hard disk drive 1540 in the image capturing system 10 via the RAM 1520, and are performed by the CPU 1505. The programs installed in the image capturing system 10 and executed by the image capturing system 10 affect the CPU 1505 to cause the image capturing system 10 to function as the image capturing section 110, the image generating section 140, the output section 180, the control section 105, the light irradiating section 150, and the like described in relation to FIGS. 1 to 10.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

What is claimed is:

1. An image capturing system, comprising:
an image capturing section that includes a plurality of first light receiving elements that receive light in a specified wavelength region and light in a first wavelength region, which is different from the specified wavelength region, and a plurality of second light receiving elements that receive light in a second wavelength region, which is different from the specified wavelength region; and
a control section that controls a spectrum of the light received by the plurality of first light receiving elements, wherein
the control section, at a first timing, causes the plurality of first light receiving elements to receive light in a wavelength region including the first wavelength region from a subject and causes the plurality of second light receiving elements to receive light in the second wavelength region and, at a second timing, causes the plurality of first light receiving elements to receive light in a wavelength region including the specified wavelength region from the subject and causes the plurality of second light receiving elements to receive light in the second wavelength region.

2. The image capturing system according to claim 1, wherein
the control section, at the first timing, causes the plurality of first light receiving elements to receive light in the first wavelength region from the subject and causes the plurality of second light receiving elements to receive light in the second wavelength region and, at the second timing, causes the plurality of first light receiving elements to receive light in the specified wavelength region from the subject and causes the plurality of second light receiving elements to receive light in the second wavelength region.

3. The image capturing system according to claim 1, further comprising an image generating section that generates a subject image at the second timing based on (i) the light in the first wavelength region received by the plurality of first light receiving elements at the first timing and (ii) the light in the second wavelength region received by the plurality of second light receiving elements at the second timing.

4. The image capturing system according to claim 3, wherein
the image generating section generates a subject image at the first timing based on (i) the light in the first wavelength region received by the plurality of first light receiving elements at the first timing and (ii) the light in the second wavelength region received by the plurality of second light receiving elements at the first timing.

5. The image capturing system according to claim 1, wherein
the control section, at the first timing, causes the plurality of first light receiving elements to receive light in the first wavelength region reflected from the subject and causes the plurality of second light receiving elements to receive light in the second wavelength region reflected from the subject and, at the second timing, causes the plurality of second light receiving elements to receive light in the second wavelength region reflected from the subject.

6. The image capturing system according to claim 5, wherein
the control section, at the first timing, (i) irradiates the subject with light in a wavelength region including the first wavelength region and the second wavelength region, (ii) causes the plurality of first light receiving elements to receive light in the first wavelength region reflected from the subject, and (iii) causes the plurality of second light receiving elements to receive light in the second wavelength region reflected from the subject and, at the second timing, (i) irradiates the subject with light in a wavelength region including the second wavelength region and (ii) causes the plurality of second light receiving elements to receive light in the second wavelength region reflected from the subject.

7. The image capturing system according to claim 6, wherein
the control section, at the second timing, (i) irradiates the subject with light in a wavelength region including the second wavelength region but not with light in the first wavelength region, (ii) causes the plurality of first light receiving elements to receive light in the specified wavelength region from the subject, and (iii) causes the plurality of second light receiving elements to receive light in the second wavelength region reflected from the subject.

8. The image capturing system according to claim 7, wherein
the control section, at the second timing, irradiates the subject with excitation light but not with light in the first wavelength region, and causes the plurality of first light receiving elements to receive light in the specified wavelength from the subject, and
the excitation light is in a wavelength region different from the first wavelength region and the second wavelength region that excites a luminescent substance inside the subject such that the luminescent substance emits light in the specified wavelength region.

9. The image capturing system according to claim 6, further comprising a plurality of light emitting elements that each emit light in a different spectrum, wherein
the control section controls irradiation of the subject with light at the first timing and the second timing by controlling emission intensity of each of the plurality of light emitting elements.

10. The image capturing system according to claim 8, further comprising:
a light emitting section that emits light in a wavelength region including the wavelength region of the excitation light, the first wavelength region, and the second wavelength region; and
an irradiation light cut filter section that allows light in the wavelength region of the excitation light and light in the second wavelength region to pass, but cuts light in the first wavelength region, wherein
the control section includes a light emission control section that irradiates the subject at the second timing with light emitted by the light emitting section through the irradiation light cut filter section.

11. The image capturing system according to claim 8, further comprising a lens-side excitation light cut filter that is disposed between the subject and the plurality of second light receiving elements, and that cuts light in the wavelength region of the excitation light, wherein
the plurality of second light receiving elements receive the light reflected from the subject via the lens-side excitation light cut filter.

12. The image capturing system according to claim 11, wherein
the lens-side excitation light cut filter cuts light in the wavelength region of the excitation light and light in the specified wavelength region.

13. The image capturing system according to claim 10, further comprising an excitation light cut filter section that allows light in a wavelength region including the first wavelength region and the second wavelength region to pass through, but cuts light in the wavelength region of the excitation light, wherein
the light emission control section irradiates the subject at the first timing with light emitted from the light emitting section through the excitation light cut filter section.

14. The image capturing system according to claim 1, wherein
the image capturing section includes a plurality of third light receiving elements that receive light in a third wavelength region, which is different from the specified wavelength region, the first wavelength region, and the second wavelength region, and
the control section, at the first timing, causes the plurality of first light receiving elements, the plurality of second light receiving elements, and the plurality of third light receiving elements to respectively receive light in a wavelength region including the first wavelength region from the subject, light in a wavelength region including the second wavelength region, and light in a wavelength region including the third wavelength region from the subject and, at the second timing, causes the plurality of first light receiving elements to receive light in a wavelength region including specified wavelength region from the subject and causes the plurality of second light receiving elements and the plurality of third light receiving elements to respectively receive light in the second wavelength region and light in the third wavelength region.

15. The image capturing system according to claim 3, wherein the image generating section includes:
a movement identifying section that identifies movement of an object between an image obtained at the first timing and an image obtained at the second timing, based on an image resulting from light in the second wavelength region received by the plurality of second light receiving elements at the first timing and an image resulting from light in the second wavelength region received by the plurality of second light receiving elements at the second timing; and
a subject image generating section that generates a subject image at the second timing, based on light in the first wavelength region received by the plurality of first light receiving elements at the first timing, light in the second wavelength region received by the plurality of second light receiving elements at the second timing, and the movement of the object.

16. The image capturing system according to claim 3, wherein the image generating section includes:
   a movement identifying section that identifies movement of an object between images obtained at a plurality of first timings, based on a plurality of images resulting from light in the first wavelength region received by the plurality of first light receiving elements at the plurality of first timings; and
   a subject image generating section that generates a subject image at the second timing, based on light in the first wavelength region received by the plurality of first light receiving elements at the plurality of first timings, light in the second wavelength region received by the plurality of second light receiving elements at the second timing, and the movement of the object.

17. An image capturing method, comprising:
   having a plurality of first light receiving elements that receive light in a specified wavelength region and light in a first wavelength region, which is different from the specified wavelength region, and a plurality of second light receiving elements that receive light in a second wavelength region, which is different from the specified wavelength region; and
   controlling a spectrum of the light received by the plurality of first light receiving elements, wherein
   the controlling involves, at a first timing, causing the plurality of first light receiving elements to receive light in a wavelength region including the first wavelength region from a subject and causing the plurality of second light receiving elements to receive light in the second wavelength region and, at a second timing, causing the plurality of first light receiving elements to receive light in a wavelength region including the specified wavelength region from the subject and causing the plurality of second light receiving elements to receive light in the second wavelength region.

18. A computer readable medium storing thereon a program for use by an image capturing system, the program causing the image capturing system to function as:
   an image capturing section including a plurality of first light receiving elements that receive light in a specified wavelength region and light in a first wavelength region, which is different from the specified wavelength region, and a plurality of second light receiving elements that receive light in a second wavelength region, which is different from the specified wavelength region; and
   a control section that controls a spectrum of the light received by the plurality of first light receiving elements and the plurality of second light receiving elements and that, at a first timing, causes the plurality of first light receiving elements to receive light in a wavelength region including the first wavelength region from a subject and causes the plurality of second light receiving elements to receive light in the second wavelength region and, at a second timing, causes the plurality of first light receiving elements to receive light in a wavelength region including the specified wavelength region from the subject and causes the plurality of second light receiving elements to receive light in the second wavelength region.

* * * * *